United States Patent [19]

Scott

[11] Patent Number: 4,992,441

[45] Date of Patent: Feb. 12, 1991

[54] 1-[[5-[[4-SUBSTITUTED-1-PIPERAZINYL]-METHYL]-PYRROL-2-YL OR FURAN-2-YL]METHYL-2-PIPERIDINONES USEFUL IN TREATING SCHIZOPHRENIA

[75] Inventor: Malcolm K. Scott, Landsdale, Pa.

[73] Assignee: McNeilab, Inc., Spring House, Pa.

[21] Appl. No.: 251,723

[22] Filed: Sep. 30, 1988

Related U.S. Application Data

[63] Continuation-in-part of Ser. No. 108,177, Oct. 14, 1987, abandoned.

[51] Int. Cl.[5] ................. A61K 31/495; A61K 31/445; C07D 401/14

[52] U.S. Cl. .................................... 514/252; 514/254; 544/364; 544/295; 546/208; 546/214

[58] Field of Search ............... 544/295, 360, 361, 364, 544/295; 514/252, 254; 546/208, 214

[56] References Cited

U.S. PATENT DOCUMENTS 4,772,604 9/1988 Van Wijngaarden .............. 514/252
4,782,061 11/1988 Kruse et al. ......................... 514/254
4,791,132 12/1988 Van Wijngaarden .............. 514/427

FOREIGN PATENT DOCUMENTS 0138280 10/1984 European Pat. Off. .
0185429 12/1985 European Pat. Off. .
0190472 12/1985 European Pat. Off. .

OTHER PUBLICATIONS

2-Phenylpyrroles as Conformationally Restricted Benazmide Analogues Class of Potential Antipsychotics, 2 Wijngaarden et al., J. Med. Chem. 1988, 31,No. 10,pp. 1934–1940.

2 Phenyl Pyrroles as Conformationally Restricted Benzamide Analogues, A New Class of Potential Antipsychotics, Wijngaarden et al., J. Med. Chem. 1987, 30, 2099–2104.

*Primary Examiner*—Cecilia Shen

[57] ABSTRACT

Mannich bases of the formula (I):

(I)

where X is oxygen or $NR^2$, Alk is divalent alkyl, $R^1$ is an aromatic ring, $R^2$ is a substituent and the salts thereof. Useful as antipsychotic agents in man to be used in a manner similar to chlorpromazine.

18 Claims, No Drawings

1-[[5-[[4-SUBSTITUTED-1-PIPERAZINYL]METHYL]-PYRROL-2-YL OR FURAN-2-YL]METHYL-2-PIPERIDINONES USEFUL IN TREATING SCHIZOPHRENIA

This is a continuation-in-part of U.S. Ser. No. 108,177, filed Oct. 14, 1987 now abandoned.

BACKGROUND OF THE INVENTION

Antipsychotic drugs are known to alleviate the symptoms of mental illnesses such as schizophrenia. Examples include phenothiazine derivatives such as promazine, chlorpromazine, fluphenazine, thioridazine and promethazine, thioxanthenes such as chlorprothixene, and butyrophenones such as haloperidol. While these agents may be effective, virtually all except clozapine produce extrapyramidal side effects such as facial tics. Since antipsychotics may be administered for years or decades to a patient, such pronounced side effects may complicate recovery and further isolate the individual from society.

An object of the invention is a potent, antipsychotic agent which preferably has a reduced tendency to induce extrapyramidal side effects compared to known agents.

SUMMARY OF THE INVENTION

Mannich bases of the following formula (I):

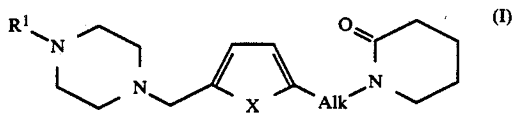

wherein X is oxygen or a substituted or unsubstituted nitrogen are potent tranquilizers for the relief of psychotic conditions in humans. Also part of the invention are pharmaceutical compositions, methods of treating psychoses, methods of synthesis and novel intermediates.

DETAILED DESCRIPTION OF THE INVENTION

The invention comprises Mannich bases of the following formula (I):

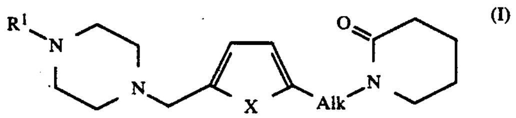

wherein

X is O or $NR^2$;

Alk is straight or branched chain alkyl;

$R^1$ is an unsubstituted or substituted aromatic ring; and $R^2$ is hydrogen, alkyl, phenylalkyl, phenyl, phenylalkyl substituted on the phenyl ring or substituted phenyl;

and the pharmaceutically-acceptable acid-addition salts thereof.

In more detail, $R^1$ may be an aromatic carbocyclic or heterocyclic ring system of about 5 to 10 members having 1, 2 or 3 oxygen, sulPhur or nitrogen atoms such as phenyl, 1,3-benzodioxolyl, pyridinyl, pyrimidinyl, quinolyl, isoquinolyl, 1,2-benzisothiazolyl, 1,2-benzisoxazolyl, indolyl, thiophenyl, furanyl, pyrrolyl, pyrazolyl, imidazolyl or triazolyl or such a ring system which is independently substituted by one or more of:

(a) alkoxy of about 1 to 6 carbons such as methoxy, ethoxy, propoxy, isopropoxy, sec-butoxy or n-butoxy;

(b) alkylthio of about 1 to 6 carbons such as methylthio;

(c) halo such as fluoro, chloro, bromo or iodo, preferably chloro or fluoro;

(d) alkyl of about 1 to 6 carbons such as methyl, ethyl, n-propyl, iso-propyl; n-butyl or tert-butyl;

(e) haloalkyl of about 1 to 6 carbons such as chloromethyl, trifluoromethyl and 2,2,2-trichloroethyl wherein the halo is fluoro, chloro, bromo or iodo, preferably fluoro or chloro;

(f) hydroxy;

(g) hydroxyalkyl of about 1 to 6 carbons such as hydroxymethyl;

(h) alkanoyl of about 2 to 6 carbons such as acetyl;

(i) alkanoyloxy of about 2 to 6 carbons such as acetoxy;

(j) cyano;

(k) phenoxy or (substituted phenyl)oxy wherein the substitution is alkyl of about 1 to 6 carbons, halo such as fluoro, chloro, bromo or iodo, alkoxy of about 1 to 6 carbons such as methoxy or isopropoxy or $CF_3$;

(l) nitro;

(m) amino;

(n) alkylamino of about 1 to 6 carbons such as methylamino;

(o) dialkylamino of about 1 to 6 carbons in each alkyl such as methylethylamino;

(p) alkanoylamino of about 2 to 8 carbons such as acetamido;

(q) sulfonamido of the formula $R^3SO_2NR^4$— wherein $R^3$ is phenyl or phenyl independently substituted by 1–3 of alkyl of about 1 to 6 carbons, halo such as fluoro, chloro, bromo or iodo, alkoxy of about 1 to 6 carbons or $CF_3$ and $R^4$ is hydrogen or alkyl of about 1 to 6 carbons, with an example being $4—CH_3C_6H_4—SO_2N(CH_3)—$;

(r) cycloalkyl of about 3 to 6 carbons, such as cyclopentyl or cyclohexyl; or (s) cycloalkyloxy of about 3 to 6 carbons, such as cyclopropyloxy or cyclohexyloxy.

When $R^1$ is a phenyl ring, the substitution may be mono and may be at the ortho, meta or para positions, particularly at the ortho position, e.g. 2-isopropoxyphenyl.

Alk in more detail may be straight or branched alkyl of about 1 to 8 carbons such as alkylene, e.g. methylene, ethylene or propylene, alkylidene, e.g. ethylidene ($CH_3CH$), or propylidene ($CH_3CH_2CH$), or 1-alkylalkylidene, e.g. 1-methylethylidene ($CH_3C(CH_3)$).

$R^2$ may be hydrogen; alkyl of about 1 to 6 carbons such as methyl, ethyl, iso-propyl or sec-butyl; phenylalkyl of about 1 to 6 carbons in the alkyl, e.g. benzyl, 2-phenylethyl or 1-phenylethyl; phenyl; or such phenylalkyl or phenyl wherein the phenyl ring is substituted with one or more substituents, e.g. 1, 2 or 3 substituents independently selected from alkyl of about 1 to 6 carbons such as methyl or ethyl, alkoxy of about 1 to carbons such as methoxy or ethoxy, halo such as fluoro, chloro, bromo or iodo or $CF_3$.

A particular subgenus of compounds of the formula (I) are those of the following formula (Ia) where X and $R^1$ are as defined for formula (I):

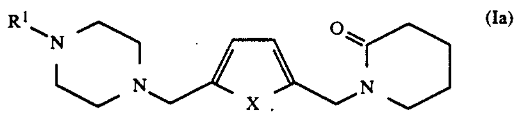

Specific examples of the compound of the invention are the following:

(1) 1-[[1-methyl-5-[[4-[2-(1-methylethoxy)phenyl]-1-piperazinyl]methyl]-1H-pyrrol-2yl]methyl]-2-piperidinone;

(2) 1-[[1-methyl-5-[[4-[2-(1-methylethyl)phenyl]-1-piperazinyl]methyl]-1H-pyrrol-2-yl]methyl]-2-piperidinone;

(3) 1-[[5-[[4-(2-methoxyphenyl)-1-piperazinyl]methyl]-1-methyl-lH-pyrrol-2-yl]methyl (4) 1-[[1-methyl-5-[[4-(3-nitrophenyl)-1-piperazinyl]methyl]-lH -pyrrol-2-yl]-methyl]-2-piperidinone;

(5) 1-[[5-[[4-(3-chlorophenyl)-1-piperazinyl]methyl]-1-methyl]-lH-pyrrol-2-yl]methyl]-2-piperidinone;

(6 ) 1-[[5-[[4-[2-(1-methylethoxy)phenyl]-1 -piperazinyl]methyl]-1H-pyrrol-2-yl]methyl]-2 -piperidinone;

(7) 1-[[5-[[4-(2-ethylphenyl)-1-piperazinyl]methyl]-1-methyl -lH-pyrrol-2-yl]-methyl]-2-piperidinone (8) 1-[[1-methyl-5-[[4-[2-(1-methylpropoxy)phenyl]-1-piperazinyl]methyl]-1H-pyrrol-2-yl]-methyl]-2-piperidinone;

(9) 1-[[5-[[4-(1,2-benzisothiazol-3-yl)-1-piperazinyl]-methyl]-1-methyl-1H-pyrrol-2-yl]methyl]-2-piperidinone;

(10) 1-[[1-Methyl-5-[[4-[2-(methoxy)phenyl]-1-piperazinyl]-methyl]-lH-pyrrol-2-yl]ethyl]-2-piperidone;

(11) 1-[[1-Methyl-5-[[4-[2-(1-methylethoxy)phenyl]-1-piperazinyl]methyl]-1H-pyrrol-2-yl]ethyl]-2-piperidone;

(12) 1-[1-[1-Methyl-5-[[4-[2-(1-methylethoxy)phenyl]-1-piperazinyl]methyl]-lH-pyrrol-2-yl]ethyl]-2-piperidinone.

As used herein, "independently" refers to the independent choice of substituents when more than one is attached, e.g. the substitutions on the R1 ring may be chloro and methoxy since the substitution is defined as being "independently" chosen. "Alkyl" groups herein are either straight or branched unless indicated otherwise. The invention definition of formula (I) and novel intermediates includes racemates and individual isomers, e.g. as caused by the presence of an asymmetric carbon such as when a substituent would be sec-butyl. Also within the scope of the invention are comPounds of the invention in the form of hydrates and other solvate forms.

Representative salts of the compounds of formula (I) which may be used include those made with acids such as hydrochloric, hydrobromic, hydroiodic, perchloric, sulfuric, nitric, phosphoric, acetic, propionic, glycolic, lactic, pyruvic, malonic, succinic, maleic, fumaric, malic, tartaric, citric, benzoic, cinnamic, mandelic, methanesulfonic, ethanesulfonic, hydroxyethanesulfonic, benzenesulfonic, p-toluene sulfonic, cyclohexanesulfamic, salicylic, p-aminosalicylic, 2-phenoxybenzoic, 2-acetoxybenzoic or a salt made with saccharin. Such salts can be made by reacting the free base of (I) with the acid and recovering the salt.

To prepare the compounds of formula (I) the reaction sequence of the following Reaction Scheme I may be used:

Reaction Scheme I

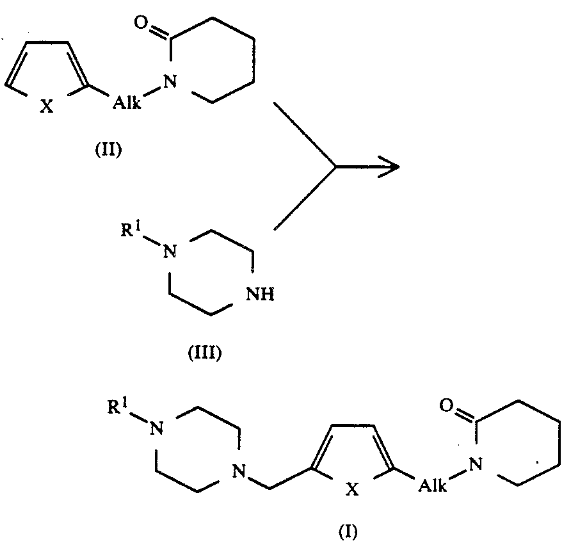

In Reaction Scheme I, Alk, X and $R^1$ are as defined for formula (I) above. In the reaction, the lactam (II) is reacted with a piperazine (III) with formalin to yield the product of formula (I).

Reaction Scheme II

To provide the starting material lactam of formula (II) where Alk is $-CH_2-$ shown below as (IIa), one may employ Reaction Scheme II as set forth below:

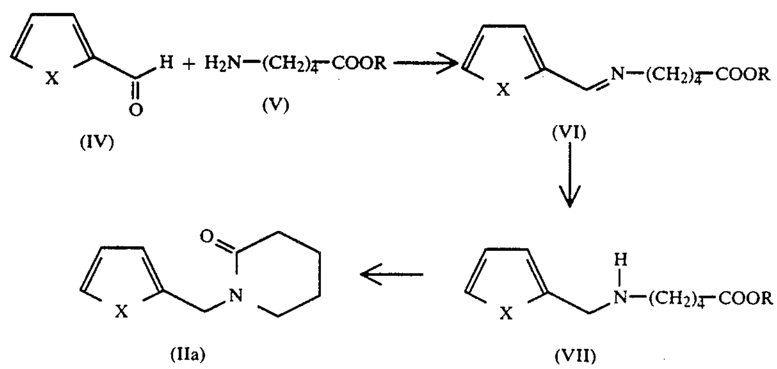

In Reaction Scheme II, X is as defined for formula (I) above. A 2-carboxaldehyde of formula (IV) is reacted with an ester of formula (V), where R is lower alkyl, under basic conditions at about 0–75° C to yield the imine (VI) which is then reduced with $H_2$ and a hydrogenation catalyst such as a nóble metal to yield the amine (VII). The amine (VII) is then cyclized by heating at about 50 to 150° C to yield the lactam (IIa) which may then be used as a formula (II) lactam in a Mannich reaction with a piPerazine (III) with formalin to yield the product of formula (I) as in Reaction Scheme I.

A second method for the synthesis of comPounds of formula (II) is summarized in the following Reaction Scheme III where X and Alk are as described for formula (I) and Y is a leaving group such as OH or halo, e.g. Cl:

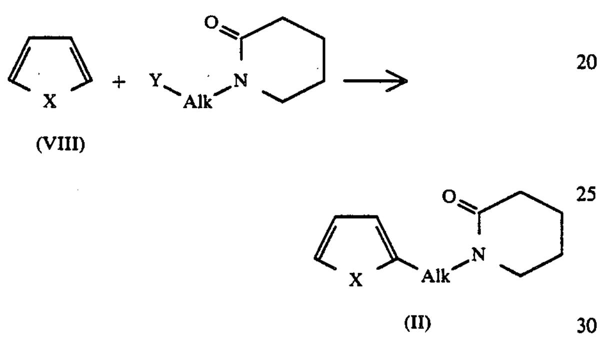

In Reaction Scheme III, a pyrrole or furan (VIII) is reacted with an amide of formula (IX) by heating neat in an excess of (VIII) or in a solvent such as trifluoroacetic acid at a temperature of about 50 to 200° C with recovery of the product (II). The product (II) may be carried on as in Reaction Scheme I.

Reaction Scheme IV

Another method of synthesizing compounds of formula (II) is set forth in the following Reaction Scheme (IV) where X is as defined for formula (I) above:

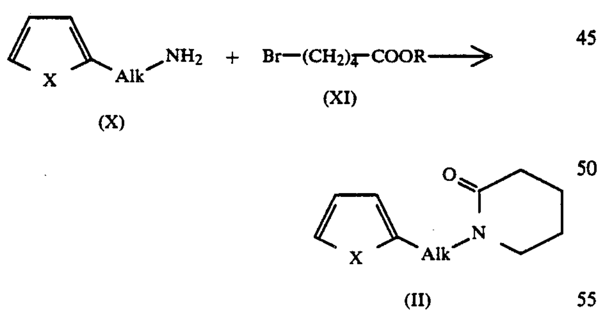

In Reaction Scheme IV, a pyrrole or furan having a 2-aminoalkyl substituent is reacted with 5-bromopentanoate where R is lower alkyl under basic conditions (to absorb the liberated HBr) in an organic solvent and heated to about 50–100° C. The condensed and cyclized product (II) may then be recovered and carried on to final product as in Reaction Scheme I.

Reaction Scheme V

The starting material piperazines of formula (III) may be obtained as known in the art or synthesized according to the following Reaction Scheme V where $R_1$ is as described for formula (I) and Z is a leaving group such as halo, e.g. chloro, or hydroxy:

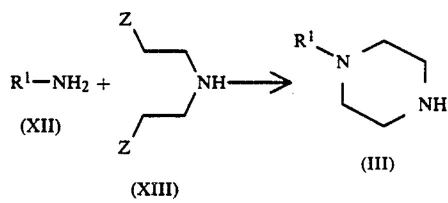

In carrying out Reaction Scheme V, an amine (XIII) is heated with an aniline or aromatic heterocyclic primary amine (XII) at about 50 to 150° C in a solvent such as n-butanol with recovery of the piperazine (III).

Reaction Scheme VI

For the lactam starting materials of formula (II) where Alk is a branched chain divalent alkyl, one may use the following Reaction Scheme VI:

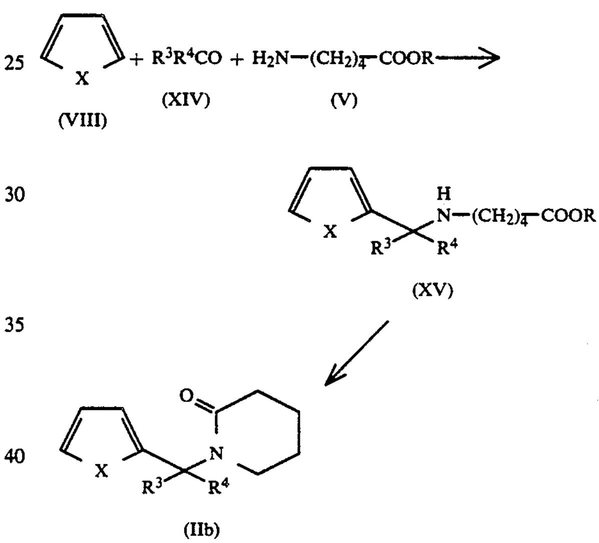

Reaction Scheme VI is a variation of Scheme II and X is as defined for formula (I), R is lower alkyl and $R^3$ and $R^4$ are hydrogen or straight or branched alkyl with the total number of carbons in $R^3$ and $R^4$ being 7 or less. In Scheme VI, the pyrrole or furan (VIII), the aldehyde or ketone (XIV) and the ester (V) are reacted at about 0 to 5° C in an inert organic solvent such as toluene and in the presence of a base such as ammonium acetate to liberate free base from the ester (V) if a salt form is used. The product (XV) is then heated at about 90 to 150° C to yield the lactam (IIb) which is then used as in Scheme I as a formula (II) lactam.

The antipsychotic activity of the compounds of the invention is indicated by the Block of Conditioned Avoidance Responding (Rat) test (CAR), references being Cook, L. and E. Weidley in Ann. N.Y. Acad. Sci., 66:740–752 (1957) and Davidson, A. B. and E. Weidley in Life Sci., 18:1279–1284 (1976). Two versions (I and II) of the CAR test are set forth below.

Block of Conditioned Avoidance Responding (Rat) I

Apparatus: Rat operant chambers, housed within sound attenuated booths, both from Campden Instruments Ltd., were used in this test. The test chamber (8"

H × 9 ⅜" W × 9" D) is constructed of aluminum and Plexiglass with floor grid bars of stainless-steel (⅛" O.D.) spaced 9/16" apart. A stainless-steel operation level 1 ½" wide projects ¾" into the chamber and is positioned 2 2/8" above the qrid floor. The shock stimulus is delivered via the qrid floor by a Coulbourn Instruments solid state module. The parameters of the test and the collection of data are controlled automatically by an Analog Device Macsym 2 computer.

Training: Male, Fischer 344 rats obtained from Charles River (Kingston, NY) weighing more than 200 g, were individually housed with chow and water provided ad libitum. The rats were trained for two weeks to approach criterion levels in the avoidance test (90% avoidance rate). One-hour training sessions were run at about the same time each day for four or five days a week. The training session consisted of 120 trials, with the conditioned stimuli presented every 30 sec. A trial begins with presentation of the conditioned stimuli (a light and a tone). If the rat responded by depressing the operant lever during the 15-second presentation of the conditioned stimuli, the trial was terminated and the animal was credited with a CAR. Failure to respond during the conditioned stimuli caused the presentation of the unconditioned stimulus, via., a 0.7 mA shock which was accompanied by a light and tone for ten seconds. If the rat depressed the lever within the ten-second period, the shock and trial were terminated and an escape response recorded. If the rat failed to depress the lever during the UCS (shock), the trial was terminated after ten sec of shock and the absence of a response was scored as a failure to escape. Intertrial level presses had no effect. If a rat performed at the 90% CAR level within two weeks, it was then run twice a week on the test schedule (see below) until baseline performance stabilized. Before any drug was administered, two weeks of CAR at a rate of 90% or better was required.

Determination of $ED_{50}$ Values

Trained rats were run in a one-hour session on two consecutive days at the same time and in the same test chamber each day. The sessions consisted of 60 trials, one every minute. The conditioned stimuli were presented for 15 sec (maximum) and the unconditioned stimulus five sec (maximum). On Day 1, a vehicle solution was administered to the rats at a time preceding the trial run corresponding to the pretreatment time for the test compound. The route of administration and the volume of vehicle were also matched to that of the test compound. Only animals that exhibited greater than 90% CAR on Day 1 were given the test compound on Day 2.

Statistical Computations: $ED_{50}$ values (that dose required to reduce the mean number of CARS to 50% of the control mean) were determined in the following manner. The percent change in CAR on the drug treatment day compared to vehicle pretreatment day was the key measure. The percent change (% change) in CAR was determined using the following formula:

% change CAR=((Day 2 % CAR/Day 1 CAR)×100)−100

A negative number indicates a blockade of CAR, whereas a positive number would indicate increased CAR. The test results are reported as the mean % change for the group of rats. Failure to escape was calculated for each animal as follows:

% Failures=# of Failures to Escape/# of trials

The % failures, viz., loss of escape, is also reported as a group mean. Failures to escape were monitored closely and a session was terminated if ten consecutive failures occurred. $ED_{50}$ values and 95% confidence limits were calculated using linear regression analysis.

The $ED_{50}$ for the oxalate product of Example lb was 11.9 mg/kg (p.o.) and 2.5 mg/kg )i.p.).

Block of Conditioned Avoidance Responding (Rat) II

Apparatus: Rat operant chambers were used in this test. The test chamber (15 ¼" H × 8 ½" W × 18 ¾" D) is constructed of plexiglass with floor grid bars of stainless-steel (7/32" O.D.) spaced 9/16" apart. This apparatus has a moveable wall (elevated 5 ¾" above the grid floor) which can be retracted to make a shelf (8 ½ " W × 5 ½"D) available to the rat. The presence of the rat on the shelf is detected by a photocell and infrared-filtered light source located 1" above the shelf and 3" from the edge. The shock stimulus is delivered through the grid floor by a Coulbourn Instruments solid state shock scrambler module. The parameters of the test and the collection of data are controlled by Coulbourn Logic Modules.

Training: Male, Sprague-Dawley rats obtained from Charles River Laboratories weighing more than 200 g were housed in groups of two with chow and water provided ad libitum. The rats were trained for three days to approach criterion levels in the avoidance test (88% avoidance rate). The training session consisted of 25 trials per animal. A trial started with a rat being placed on the grid floor of the apparatus. After ten sec, the wall retracted, making a shelf available to the animal. Retraction of the wall was considered to be the CS. If the animal did not respond to the CS within 10 sec by jumping onto the shelf, the UCS, an electric shock (7 mA), was delivered through the floor for 10 sec (0.25 sec, shock on; 0.75 sec, shock off). Jumping onto the shelf before the shock-period began was counted as a CAR. If the rat failed to avoid the shock but jumped onto the shelf during the UCS (shock), an escape response was recorded. If the rat failed to avoid the shock and also failed to jump onto the shelf during the UCS, an escape failure was recorded.

Testing: Rats were given the vehicle on the third training day and were tested one and four hr later. Animals with a mean CAR rate of 88% or better in the two test sessions were selected as test subjects. Thus, the day that a rat was given the vehicle and entered into the study was defined as Day-1 of the test. The vehicle solution was administered to the subject at a time Preceding the trial that corresponded to the pretreatment time for the test compound. The route of administration and the volume of the vehicle were also matched to that of the test compound. Test compounds were administered on the following day (Day-2 of the test) and trained rats were tested (two sessions, each 25 trials) at the same time and in the same chamber as previously.

Criterion of Efficacy: Since animals tested on the vehicle day (Day-1) or tested after receiving the vehicle on the experimental day (Day-2) never made less than 20 CARs, treatment effects were considered positive in animals making less than 20 avoidance responses (less than 80% CAR rate) during each test session. Thus, a treatment was rated as active if the mean CAR rate in the treatment-group was less than 80%.

Measure of Specificity: One of the characteristic behavioral effects of neuroleptics is suppression of the CAR at doses that do not interfere with the ability of animals to escape the UCS (foot shock). Failure to escape the shock for each drug treated animal was calculated by the following formula:

Escape Failure=(Number of escape failures/Number of trials in the session

A test for the occurrence of extrapyramidal side effects is the Catalepsy (Rat) test with a reference being Clineschmidt, B. V. et al. in J.P.E.T., 208, pages 460–467 (1979).

Catalepsy (Rat)

Male Sprague-Dawley rats obtained from Charles River (Kingston, N.Y.), n=6–8 dose, weighing 170–240 g were used. At least three doses of test drug were used to determine the $ED_{50}$ value for production of catalepsy. The rat's forepaw was gently placed on a black cork (3.5 cm high) and the time until the forepaw was removed was recorded.

Each rat was given three trials on the cork with the sum of three trials taken as the rat's score. Percent catalepsy was defined as the percent of 180 (maximum) seconds that a rat permitted its forepaw to rest on the cork. The experiment was conducted in a quiet room, with the experimenter unaware of the drug or dose level administered. The test drug was administered in at least three concentrations. A vehicle-treated group (n=6–8) served as controls. Prior to determining $ED_{50}$ values, the time of peak effect from each drug was determined by giving a group of rats (n=6–8) a dose estimated to be greater than each compounds $ED_{50}$ from CAR experiments. Catalepsy was measured at 30, 60, 90 and 120 min post-injection. The drug's dose-response was then determined at the time at which the greatest amount of catalepsy was observed in this pilot study. A least squares linear regression analysis was then performed to determine $ED_{50}$ values, viz., that dose which would Produce a mean catalepsy score of 90 sec, and 95% confidence limits using the EDPLOT Program.

The catalepsy value for the oxalate product of Example 1b was 11% at 25 mg/kg (i.p.), 10 times its $ED_{50}$ in the CAR.

The Bar Method: In addition to using the cork method, the test compound may also be tested for catalepsy production using the bar method. in this paradigm, the rat's front paws are placed on a steel rod situated 10 cm above and parallel to the bench top. The time it takes the animal to withdraw its paws is measured with a cut-off time of 60 seconds. The sum of three consecutive placements (seconds) divided by 180 seconds (max) × 100 was taken as a percent catalepsy score for each rat.

The compounds of the invention may be used in pharmaceutical compositions comprising a pharmaceutically-effective, e.g. an anti-psychotically effective amount, of a compound of formula (I) in combination with a pharmaceuticallY-acceptable diluent or carrier. For treatment of a mammal, e.g. a human, an amount of about 50 to 500 mg per day, based on a weight of about 50 kg. The regimen for a human would be about the same as chlorpromazine.

To prepare the pharmaceutical compositions of this invention, one or more compounds or salt thereof of the invention as the active ingredient, is intimately admixed with a pharmaceutical carrier according to conventional pharmaceutical compounding techniques, which carrier may take a wide variety of forms depending on the form of preparation desired fro administration, e.g., oral or parenteral. In preparing the compositions in oral dosage form, any of the usual pharmaceutical media may be employed. Thus for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage until form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, from about 50 to about 100 mg of the active ingredient.

In the following Examples and throughout the specification, the following abbreviations may be used: Ho (Hoover); mg (milligrams); g (grams); kg (kilograms); 1 (liters); mL (milliliters); mmole (millimoles); m (moles); N (normal); mp (melting point); bp (boiling point); E (trans); Z (cis); H (height); W (width); D (depth); o.d. (outside diameter); CAR (conditioned avoidance response); CS (conditioned stimulus); UCS (unconditioned stimulus); mA (milliampere); $Et_{20}$ (diethyl ether); EtOAc (ethyl acetate); MeOH (methanol); EtOH (ethanol); THF (tetrahydrofuran); DMF (N,N-dimethylforamide); hplc (high pressure liquid chromatography); v/v (volume to volume ratio); hr (hours); min (minutes); sec (seconds); i.p. (intraperitoneally); p.o. (per os, orally); mg/Kg (mg per Kg of body weight). Unless otherwise indicated, all temperatures are reported in °C (degrees centigrade).

EXAMPLE 1 a. 1-(1-Methylpyrrol-2-ylmethyl)-2-piperidinone

A mixture of N-methylpyrrol-2-carboxaldehyde (52.22 g, 0.48 mole), 5-aminovaleric acid methyl ester hydrochloride (80.0 gm 9,47 mole), 5A molecular sieves (212 g), and chloroform (1000 mL) was treated slowly with triethylamine (204 mL) resulting in a slight exotherm. The reaction mixture was stirred overnight under nitrogen at 25° C after which it was filtered through diatomaceous earth, and evaporated to a semisolid residue. This was slurried in $Et_2O$, filtered and evaporated to give an orange oil, 108.4 g. Reduction of this material (36.0 g portions, 0.75 g platinum oxide, and 225 mL ethanol) afforded a yellow semisolid which was slurried in $Et_{20}$ and filtered to give 98.04 g of light yellow oil. A solution of this material (98.04 g, 0.438 mole) and 980 mL of toluene was refluxed 8 hr under a nitrogen atmosphere and then the solvent was evaporated. Distillation of the residue gave 60.24 g of 1-(1-methylpyrrol-2-ylmethyl)-2-pyrrolidinone as clear oil, bp 125–130° C at 0.35 mm of Hg, which slowly crystallized. Recrystallization of 3.0 g of this material from $Et_2O$-hexane afforded 1.95 g of the title product as a light, yellow crystalline solid, mp 44.5–47.5° C. (Ho, uncorrected).

b.
1-[[1-Methyl-5-[[4-[2-(1-methylethoxy)phenyl]-1-piperazinyl]methyl]-1H-pyrrol-2-yl]methyl]-2-piperidinone A solution of 1-[2-(1-methylethoxy)phenyl]piperazine (9.38 g, 0.043 mole) as described in U.S. Pat. Nos. 4,547,505 and 4,438,115, glacial acetic acid (2.57 mL, 0.043 mole), and methanol (27 mL) was cooled in an ice bath and treated with 37% formalin (3.18 mL, 0.043 mole). A solution of 1-(1-methylpyrrol-2-ylmethyl)-2-piperidinone (8.19 g, 0.043 mole) and methanol (27 mL) was added and the resulting solution was stirred overnight at 25° C under a dry nitrogen atmosphere. Methylene chloride (350 mL) was added followed by 3N sodium hydroxide solution (60 mL). After thorough mixing, the organic layer was separated, dried over anhydrous potassium carbonate, filtered and evaporated to give 18.20 g of 1-[[1-methyl-5-[[4-[2-(1-methylethoxy)phenyl]-1 -piperazinyl]methyl]-lH-pyrrol-2-yl]methyl]-2- piperidinone as a Yellow oil. This material (2.50 g) was dissolved in 6 mL ethanol and treated with 0.68 g of oxalic acid. The mixture was heated to effect solution, cooled and ether added until just cloudy. After cooling in an ice bath, a white solid was obtained by filtration. This was recrystallized twice from ethanol-ether using activated charcoal to give the oxalate salt, mp 139.5–140.5° C (Ho).

EXAMPLE 2 a. 1-[2-(Methylethyl)phenyl]piperazine

A mixture of bis(2-chloroethyl)amine hydrochloride (19.78 g, 0.111 mole) and 200 mL of n-butanol was treated dropwise with 2-isopropylaniline (15.0 g, 0.111 mole) and the resulting mixture was stirred for 48 hr at reflux under an argon atmosphere. After cooling to room temperature, anhydrous sodium carbonate (5.86 g, 0.555 mole) was added and the reaction mixture was stirred for another 24 hr at reflux. The reaction was cooled in ice and a white precipitate was filtered off. This material was mixed thoroughly in methylene chloride and 3N sodium hydroxide until the aqueous layer was basic. The methylene chloride layer was separated, dried over anhydrous potassium carbonate, filtered and evaporated affording 6.82 g of 1-[2-(methylethyl)-phenyl]piperazine as an oil. The fumarate acid salt was prepared from isopropanol/methanol and recrystallized from methanol to give a white crystalline solid, mp 188–189° C (Ho).

b.
1-[1-Methyl]-5-[[4-[2-(1-methylethyl)phenyl]-1-piperazinyl]methyl]-1H-pyrrol-2-yl]methyl]-2-piperidinone (Z)-2-Butenedioate The Procedure of Example lb was repeated with an equimolar amount of the piperazine of Example 2a in the place of -[2-(1-methylethoxy)Phenyl]piperazine to yield the title product using isopropanol as a recrystallization solvent, mp 141.5–144° C (Ho).

EXAMPLES 3–9

The procedures of Examples 1 and 2 may be repeated with variation of the starting material of formula (II) and/or (III) to yield the following products of formula (I). For example, 1-[2-(1-methylpropoxy)phenyl]piperazine may be prepared as a fumarate salt, mp (sinter 120° C) 134–137° C (Ho). The recrystallization solvents are indicated in parentheses:

(3) 1-[[5-[[4-(2-Methoxyphenyl)-1-piperazinyl]methyl]-1-methyl-lH-Pyrrol-2-yl]methyl]-2-piperidinone; (Z)-2-Butenedioate (isopropanol); mp 141.5–143.5° C (Ho);

(4) 1-[[1-Methyl-5-[[4-(3-nitrophenyl)-1-piperazinyl]-methyl]-lH-pyrrol-2-yl]-methyl]-2-piperidinone: mp 140.0–141.5° C;

(5) 1-[[5-[[4-(3-Chlorophenyl)-1-piperazinyl]methyl]-1-methyl-lH-pyrrol-2-yl]methyl]-2-piperidinone Ethanedioate Hydrate (5:5:2); mp 130° C (decomposition) (isopropanol);

(6) 1-[[5-[[4-[2-(1-methylethoxy)phenyl]-1-piperazinyl]-methyl]-lH-Pyrrol-2-yl]methyl]-2-piperidinone Ethanedioate Hydrate (2:2:1); mp (153° darkens sl.) 156.0–157.5° C (Ho) (MeOH $Et_2O$);

(7) 1-[[5-[[4-(2-Ethylphenyl)-1-piperazinyl]methyl]-1-methyl-lH-pyrrol-2-yl]-methyl]-2-piperidinone [R-(R*,R*)]-2,3,-Dihydroxybutanedioate Hydrate (20:27:14); mp 70° C (Ho, with foaming) (EtOH-$Et_2O$);

(8) 1-[[1-Methyl-5-[[4-[2-(1-methylpropoxy)phenyl]-1-piperazinyl]methyl]-lH-pyrrol-2-yl]-methyl]-2-piperidinone [R-(R*,R*)]-2,3-DihydrOxybutanedioate Hydrate (5:5:2) mp 153–154° C (EtOH $Et_2O$);

(9) 1-[[5-[[4-(1,2-Benzisothiazol-3-yl)-1-piperazinyl]-methyl]-1-methyl-lH-pyrrol-2-yl]methyl]-2-piperidinone [R-R*,R*)]-2,3-Dihydrobutanedioate 2-propanolate hydrate (10:13:10:6); mp 96° C (Ho, dec) (isopropanol).

EXAMPLE 10 a. 1-[2-(1-Methyl-lH-pyrrol-2-yl)ethyl]-2-piperidone 2-(1-Methylpyrrol-2-yl)ethylamine (4.96g, 0.04m) and triethylamine (5.6mL, 0.04m) were stirred together in toluene (60mL). A solution of ethyl 5-bromopentanoate (7.80g, 0.04m) in toluene (20 mL) was added dropwise over 1 hr at room temperature. The reaction mixture was heated with stirring at 70 degrees overnight. The reaction was worked up by addition of a phosphate buffer until a pH of 5–6 was reached; the reaction mixture was then diluted with ether and the layers were separated. The aqueous layer was exhaustively washed with diethyl ether. The combined organic layers were washed with water, brine and then dried over anhydrous potassium carbonate. The dryinq agent was filtered away, and the filtrate was concentrated to a light yellow solid weighing 5.2g. It was recrystallized from methylene chloride/hexane to give 4.2g (51.2%) of purified title compound.

b. 1-[[1-Methyl-5-[[4[-2-(methoxy)phenyl]-1-piperazinyl[methyl]-lH-pyrrol-2-yl]ethyl]-2-piperidone Hydrochloride A solution of the acetate salt of 1-[2-(methoxy)-phenyl]Piperazine (2.52g, 0.01m) in methanol (8mL), while stirring under a nitrogen atmosPhere, was treated with acetic acid (2 drops). Formalin (0.8mL, 37% solution) was added, followed by a solution of 1-(1-methylpyrrol-2-ylethyl) -2-piperidone (2.06g, 0.01m), the product of Example 10*a*, in MeOH (8mL). After stirring at room temperature for four and one half hr, the reaction aPpeared completed by tlc. The reaction mixture stirred at room temperature overnight; tlc looked the same upon standing.

The reaction was worked up by dilution with methylene chloride (80mL), followed by treatment with sodium hydroxide (lN, 30mL) with vigorous stirring. The layers were separated and the aqueous layer was extracted with methylene chloride (15mL) twice. The combined organic layers were washed with brine and then treated with hydrochloric acid (llmL, lN). The organic layer was separated, washed with brine and dried over anhydrous magnesium sulfate. The suspension was filtered, the filtrate was concentrated and dried in vacuo. The dried residue weighed 4.lg. Proton NMR indicated the product to be the desired title compound. It was recrystallized by dissolution in hot isopropanol (12mL), treatment with $Et_2O$ to the cloud point and then coolinq at 0° C. The product was collected by filtration to give 3.3g of product. The purified hydrochloride salt had a mp of 173° C.

EXAMPLE 11

1-[[1-Methyl-5-4-2-(1-methylethoxy)phenyl]-1-piperazinyl]methyl]-lH-pyrrol-2-yl]ethyl]-2-piperidone Hydrochloride The Procedure of Example 10b was repeated substituting an equivalent amount of 1-[2-(1-methylethoxy)-phenyl]-piperazine for 1-[2-(methoxy)phenyl]piperazine, carrying out the additions at 0° C and then allowing the reaction to warm to room temperature. After a similar work up, the title compound was obtained with a mp of 177° C.

EXAMPLE 12 a. 5-1-(1-methylpyrrole-2-vl)ethyl]aminovalerate

To a solution freshly redistilled N-methylpyrrole (0.81g, 0.01m) in acetic acid (5mL) at 0° C was added methyl 5-aminovalerate hydrochloride salt (1.67g, 0.01m) and ammonium acetate (0.77g, 0.01m) with stirring in nitrogen atmosPhere. Then over 10 min an ice-cold solution of acetaldehyde (0.44g, 0.01m) in toluene (2mL) was added dropwise. Stirring was continued for 2 hr and the flask stored in a refrigerator for 3 days. The contents were Poured into a mixture of ice-cold water (5mL) and ether (2mL). The ether layer was separated and washed once with aqueous $KH_2PO_4$ solution. The combined aqueous solutions were chilled and adjusted to pH 7 with 30% NaOH solution at a temperature not exceeding 20° C and filtered. The filtrate was made basic and extracted exhaustively with methylene chloride. The combined extracts were washed once with brine and dried over anhydrous potassium carbonate. The drying agent was filtered away and the filtrate was concentrated to give 0.91g of title compound.

b. 1-]1-(1methyl 1H-pyrrol-2yl)ethyl]-2piperidone

Heating the product of Example 12a at 110–150° C in a solvent (e.g. toluene, xylene) gives the title compound.

c.

c. 1-1-1-Methyl-5-[[4-[2-(1-methylethoxy)phenyl]-1-piperazinyl]methyl]-lH-pyrrol-2-yl]ethyl]-2-piperidinone The procedure of Example lb may be repeated with the product of Example 12b being used in the place of 1-(1-methylpyrrol-2-ylmethyl)-2-piperdinone to yield the title product.

What is claimed is:

1. A Mannich base of the following formula (I):

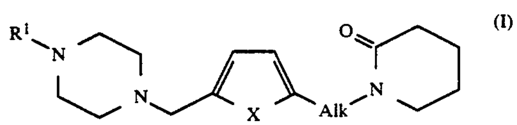

X is 0 or $NR^2$;

Alk is a a straight or branched chain divalent alkyl of 1–8 carbons;

$R_1$ is an unsubstituted or substituted phenyl ring or an unsubstituted or substituted aromatic heterocyclic ring system selected from the group consisting of:

1,3-benzodioxolyl,
pyridinyl,
pyrimidinyl
quinolyl,
isoquinolyl,
1,2-benzisoxazolyl,
indolyl,
thiophenyl,
thiophenyl,
furanyl,
pyrrolyl, pol pyrazolyl,
imidazolyl, or
triazolyl and said substitution on said phenyl ring or aromatic heterocyclic ring of $R^1$ is independently one or more of:

alkoxy of 1 to 6 carbons;
alkylthio of 1 to 6 carbons;
Halo,
alkyl of 1 to 6 carbons;
hydroxy;
hydroxyalyl of about 1 to 6 carbons;
alkanoyl of abut 2 to 6 carbons;
alkanoyloxy of about 2 to 6 carbons;
cyano;
phenoxy or (substituted phenyl)oxy wherein the substitution if aklyl of 1 to 6 carbons, halo, alkoxy of about 1 to 6 carbons or $CF_3$;
nitro;
amino;
alkylamino of 1 to 6 carbons;
dialkylamino of 1 to 6 carbons in each alkyl;
alkanoylamino of 2 to 8 carbons;
sulfonamido of the formula $R^3SO_2NR^4$
where $R^3$ is phenyl or phenyl independently substituted by one or more of alkyl of 1 to 6 carbons, halo, alkoxy of 2 to 6 carbons or $CF_3$ and $R^4$ is hydrogen or alkyl of 1 to 6 carbons;
cycloalkyl of 3 to 6 carbons, or
cycloakyloxy of 3 to 6 carbons. and $R_2$ is hydrogen, alkyl of 1–6 carbons, phenylalkyl of 1–6 carbons, phenyl, phenylalkyl of 1–6 carbons substituted on the phenyl ring or substituted phenyl, wherein the phenyl is substituted with one or more substituents selected from alkyl of 1 to 6 carbons, alkoxy of 1 to 6 carbons in halo; or a pharmaceutically-acceptable salt thereof.

2. The Mannich base of claim 1, wherein $R^1$ is an unsubstituted or substituted phenyl ring.

3. The Mannich base of claim 1, wherein $R^2$ is alkyl of 1 to 6 carbons.

4. The Mannich base of claim 1, wherein $R^1$ is a phenyl ring mono-substituted at the ortho position.

5. The Mannich base of claim 1, wherein $R^1$ is a mono-alkoxy substituted phenyl and wherein said alkoxy group is substituted at the ortho position.

6. The Mannich base of claim 5, wherein said alkoxy group is substituted at the ortho position.

7. The Mannich base of claim 1 wherein Alk is straight or branched chain divalent alkyl of 1 to 8 carbons.

8. The Mannich base of claim 1, wherein
X is $NR^2$;
$R^1$ is a substituted phenyl ring; and
$R^2$ is alkyl.

9. The Mannich base of claim 1, wherein X is $NR^2$.

10. The Mannich base of claim 1, wherein said base is
1-[[1-methyl-5-[[4-[2-(1-methylethoxy)phenyl]-1-piperazinyl]methyl]-1H-pyrrol-2-yl]methyl]-2-piperidinone;
1-[[1-methyl-5-[[4-[2-(1-methylethoxy)phenyl]-1-piperazinyl]methyl]-1H-pyrrol-2-yl]methyl]-2-piperidinone;
1-[[5-[[4-(2-methoxyphenyl)-1-piperazinyl]methyl]-1-methyl-1H -pyrrol-2-yl]methyl]-2-piperidinone;
1-[[1-methyl-5-[[4-(3-nitrophenyl)-1-piperazinyl]-methyl]-1H -pyrrol-2-yl]-methyl]-2-piperidinone;
1-[[5-[[4-(3-chlorophenyl)-1-piperazinyl]methyl]-1-methyl -1H-pyrrol-2-yl]methyl]-2-piperidinone;
1-[[5-[[4-[2-(1-methylethoxy)phenyl]-1-piperazinyl]methyl]-1H -pyrrol-2-yl]methyl]-2-piperidinone;
1-[[5-[[4-(2-ethylphenyl)-1-piperazinyl]methyl]-1-methyl -1H-pyrrol-2-yl]-methyl]-2-piperidinone;
1-[[1-methyl-5-[[4-[2-(1-methylpropoxy)phenyl]-1-piperazinyl]methyl]-1H -pryyol-2-yl]-methyl]-2-piperidinone;
1-[[5-[[4-(1,2-benzisothiazol-3-yl)-1-piperazinyl]-methyl]-1-methyl -1H-pyrrol-2-yl]methyl]-2-piperidinone;
1-[[1-methyl-5-[[4-[2-(1-methylethoxy)phenyl]-1-piperazinyl]-methyl]-1H-pyrrol -2-yl]ethyl]-2-piperidone;
1-[[1-methyl-5-[[4-[2-(1-methylethoxy)phenyl]-1-piperazinyl]methyl]-1H -pyrrol-2-yl]ethyl]-2-piperidone; or
1-[1-[1-Methyl-5-[[4-[2-(1-methylethoxy)phenyl]-1-piperazinyl]methyl]-1H -pyrrol-2-yl]ethyl]-2-piperidinone
or a pharmaceutically-acceptable, acid-addition salt thereof.

11. The Mannich base of claim 1, wherein said base is 1-[[1-methyl-5-[[4-[2-(1-methylethoxy) phenyl[-1-piperazinyl[methyl[-1H-pyrrol-2-yl[methyl[-2-piperidinone or a pharmaceutically-acceptable salt thereof.

12. The Mannich base of claim 1, wherein said base is a pharmaceutically-acceptable salt of 1-[[1-methyl-5-[[4-[2-(1-methylethoxy)phenyl[-1-piperazinyl]methyl]-1H-pyrrol-2-yl]methyl]-1H-pyrrol-2-yl]methyl]-2-piperidinone.

13. The Mannich base of claim 1, wherein said substitution on said phenyl ring or aromatic hetrocyclic ring of $R^1$ is a single substitution.

14. A Mannich base of the following formula (Ia):

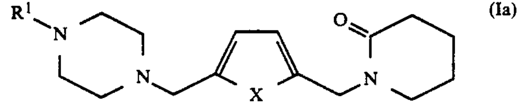

(Ia)

X is O or $NR^2$;

$R_1$ is an unsubstituted or substituted aromatic ring; is an unsubstituted or substituted phenyl ring or an unsubstituted or substituted aromatic heterocyclic ring system selected from the group consisting of:
1,3-benzodioxolyl,
pyridinyl,
pyrimidinyl
quinolyl,
isoquinolyl,
1,2-benzisoxazolyl,
indolyl,
thiophenyl,
thiophenyl, pol furanyl,
pyrrolyl,
pyrazolyl,
imidazolyl, or
triazolyl
and said substitution on said phenyl ring or aromatic heterocyclic ring of $R^1$ is independently one or more of:
alkoxy of 1 to 6 carbons;
alkylthio of 1 to 6 carbons;
Halo,
alkyl of 1 to 6 carbons;
haloalkyl of 1 to 6 carbons;
hydroxy;
hydroxyalkyl of about 1 to 6 carbons;
alkanoyl of abut 2 to 6 carbons;
alkanoyloxy of about 2 to 6 carbons,
cyano;
phenoxy or (substituted phenyl)oxy wherein the substitution if aklyl of 1 to 6 carbons, halo, alkoxy of about 1 to 6 carbons or $CF_3$;
nitro;
amino;
alkylamino of 1 to 6 carbons;
dialkylamino of 1 to 6 carbons in each alkyl;
alkanoylamino of 2 to 8 carbons;
sulfonamido of the formula $R^3SO_2NR^4$
where $R^3$ is phenyl or phenyl independently substituted by one or more of alkyl of 1 to 6 carbons, halo, alkoxy of 2 to 6 carbons or $CF_3$ and $R^4$ is hydrogen or alkyl of 1 to 6 carbons;
cycloalkyl of 3 to 6 carbons, or
cycloakyloxy of 3 to 6 carbons. and
$R_2$ is hydrogen, alkyl of 1-6 carbons, phenylalkyl of 1-6 carbons, phenyl, phenylalkyl of 1-6 carbons substituted on the phenyl ring or substituted phenyl,
wherein the phenyl is substituted with one or more substituents selected form alkyl of 1 to 6 carbons, alkoxy of 1 to 6 carbons in halo; or a pharmaceutically-acceptable salt.

15. A pharmaceutical composition for use in treating psychosis which comprises the Mannich base of claim 1 in an antipsychotic effective amount in combination with a pharmaceutically-acceptable diluent or carrier.

16. A method for the treatment of schizophrenia which comprises administering to a mammal in need thereof, the pharmaceutical composition of claim 15.

17. A compound of the following formula (II):

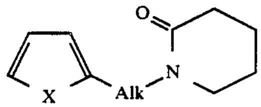

(II)

wherein

X is O or $NR^2$;

Alk is straight or branched chain divalent alkyl of 1–8 carbon atoms;

$R^2$ is hydrogen, alkyl of 1–6 carbons, phenylalkyl of 1–6 carbons, phenyl, phenylalkyl of 1–6 carbons substituted on the phenyl ring or substituted phenyl, wherein the phenyl is substituted with one or more substituents selected from alkyl of 1 to 6 carbons, alkoxy of 1 to 6 carbons in halo; or a pharmaceutically-acceptable salt thereof.

18. The compound of claim 16, wherein said compound is 1-(1-methylpyrrol-2-ylmethyl)-2-piperidinone.

* * * * *